United States Patent [19]

Higo et al.

[11] Patent Number: 4,751,184

[45] Date of Patent: Jun. 14, 1988

[54] SELECTIVE TEST PACK FEEDER FOR BIOCHEMICAL ANALYZING APPARATUS

[75] Inventors: Yuji Higo, Nagoya; Hidechika Hayashi, Yokohama, both of Japan

[73] Assignee: Tosoh Corporation, Yamaguchi, Japan

[21] Appl. No.: 70,766

[22] Filed: Jul. 7, 1987

[30] Foreign Application Priority Data

Jul. 7, 1986 [JP] Japan ................................ 61-159470

[51] Int. Cl.$^4$ .............................................. C12M 1/00
[52] U.S. Cl. ................................... 435/287; 435/293; 53/493; 436/809; 422/65
[58] Field of Search ........................ 435/287, 292, 293; 422/63, 65, 67, 73; 53/246, 493; 414/416; 73/863; 436/43, 809

[56] References Cited

U.S. PATENT DOCUMENTS 3,660,638  5/1972  Oberli .................................... 422/67
3,897,216  7/1975  Jones ..................................... 422/67
4,483,927  11/1984  Takekawa ............................. 422/67

Primary Examiner—Samuel Scott
Assistant Examiner—Noah P. Kamen
Attorney, Agent, or Firm—Sughrue, Mion, Zinn, Macpeak and Seas

[57] ABSTRACT

Sealed analyte test packs or cups 11 disposed in holding trays 21 arrayed in a drawer 42 are individually and selectively transferred to a carrying tray 43 at a coplanar loading station for subsequent conveyance to an automated biochemical analyzing apparatus. An x/y scanning mechanism 46 is disposed above the drawer and tray to implement the transfers using a vacuum head 50 mounted on a movable plate 47 of the mechanism which is lowered onto the seal of a selected test pack and then raised to remove the pack from its holding tray. The plate also mounts an IR photo reflector 49 for detecting the test packs and a bar code sensor 48 for reading the holding tray labels. The array of trays is initially scanned to read their labels and establish a location map in a computer memory, which is subsequently updated during the transfer operations.

2 Claims, 3 Drawing Sheets

SELECTIVE TEST PACK FEEDER FOR BIOCHEMICAL ANALYZING APPARATUS

BACKGROUND OF THE INVENTION

1. Field of the Invention

The present invention relates to a selective test pack feeder which can be advantageously used to supply test packs (reaction vessels providing reaction chambers for different analysis items) to any automatized analyzing apparatus that can perform biochemical analyses such as immuno-chemical analysis.

2. Description of the Prior Art

Two types of operating methods have been conventionally known for biochemical analyses such as immuno-chemical analysis; in a first method a reagent for each analyte, contained in a given vessel set in an analyzing apparatus, is fractionally poured into reaction vessels of specimens during an analyzing operation, and in a second method a common reagent is fractionally poured into individual reaction vessels containing different reagents for the corresponding analytes when the analysis is made.

Recent circumstances have required a process for analyzing a number of specimens on a mass production basis. For instance, a biochemical analysis in a narrow sense, or an immuno-chemical analysis recently has been widely used for the diagnoses of diseases, as the number of analytes as well as the number of assays processed by clinical laboratories has increased.

Under these circumstances, automatized multi-analyte biochemical analyzing apparatuses in a narrow sense, or immunochemical analyzing apparatuses (hereinafter referred to as "biochemical analyzing apparatuses") using the first method as described above have been provided.

These apparatuses have been generally used in such a way that every analyte was analyzed on each specimen in sequence.

While the analytes were more diversified, the medical costs have been higher and higher. In these circumstances, the practices of making an analysis on all analytes have been considered to be useless or wasteful in these biochemical analyzing apparatuses and their operations from the viewpoint of practical purposes. Consequently, needs have been increased for analytical processing wherein each of many specimens is analyzed on selected analytes as required (hereinafter referred to as "random access processing").

To satisfy these increasing needs, random access processing apparatuses using the first method have been provided. However, the efficiency in apparatus and reagent has deteriorated, as the range of measuring analytes as well as the range of differences in measuring frequency between analytes has enlarged.

On the other hand, more and more attention has been directed to biochemical anlayzing apparatuses using the second method, which are suitable to random access processing involving a wide range of measuring analytes as well as a wide range of differences in measuring frequency between analytes.

However, random access processing as described above requires feeding in analyzing apparatus with multiple types of test packs in independent analyzing orders on specimens. This requirement makes the analyzing works complicated and onerous and consequently causes erroneous operation.

SUMMARY OF THE INVENTION

From these points of view, an object of the present invention is to provide a selective test pack feeder which can provide a mechanized and automatized operation for loading a carrying tray with test packs at random to meet any random analysis requirements as described above.

Another object of the present invention is to provide a selective test pack feeder which can select and load test packs onto a carrying tray efficiently without any erroneous operation and which is highly suitable to any multi-analyte biochemical analyzing apparatus.

To attain these objects of the present invention, the selective test pack feeder for any biochemical analyzing apparatus comprises a channel in which a carrying tray for holding a matrix of test packs is transported and which is equipped with means for stopping the carrying tray at a loading position; a test pack drawer in which multiple types of test pack trays holding many arrays of the same type test packs and labelled with the mark of the test pack type on the top surface of the tray are placed in a plane on about the same level with the transporting channel; an x/y scanning mechanism disposed over both the transporting channel and the test pack drawer and equipped with a movable scanning body driven by a driving mechanism to make an x/y scan; and an input unit to specify the loading sequence of test packs onto the carrying trays. The apparatus is characterized by means for removably suspending a test pack and optical detecting means for detecting the presence of any test pack and reading the mark of the test pack type mounted on the movable scanning body on the x/y scanning mechanism. The feeder also comprises an electronic control unit which has an input connected to the optical detecting means and the input unit to specify the loading sequence of test packs and an output connected to the x/y scanning mechanism, the suspending or transferring means and the stopping means of the channel in order to control the loading of test packs.

The marking of test pack type may be provided, for example, by using a bar code, digits, letters or other signs, whichever are applicable. In addition to the marking, any labelling of lot numbers or other information may be provided as required.

The carrying tray used in the feeder according to the present invention may be sufficient, if it can hold and carry arrays of test packs. However, it is generally preferable that the carrying tray is a plate provided with many holes in arrays to accommodate test packs in them.

It is generally desirable that the channel to transport the carrying tray in it is equipped with an intermittent feed mechanism which permits stopping the tray at the test pack loading position. Therefore, the feeder according to the present invnetion is equipped with an intermittent feed mechanism in addition to the feed mechanism. The intermittent feed mechanism may be the feed mechanism which provides also an intermittent feed operation, or which is provided with means to provide a frictional transportation of the carrying tray, for example, by using a revolving belt as well as stopper means to engage with a carrying tray for stopping it.

The x/y scanning mechanism placed over both the transporting channel and the test pack drawer is provided with a vacuum head and an optical detector. This mechanism may be preferably one which can provide a smooth operation to transfer test packs between the test pack tray and the carrying tray.

The vacuum head removes any test pack on a given test pack tray and transfers it onto the carrying tray in the holding part thereof at a given position. Since the test pack used according to the present invention is generally as light as 10 g at most, the vacuum head generally comprises a vacuum pad to attract the top face seal of a test pack, and a mechanism to lift the pad.

The optical detecting means as described above comprises a first reading means for the marking on a test pack tray and a second reading means to detect the presence of any test pack by the reflected rays of light from the top seal of the test pack. These means are preferably small sized, and may be composed of any known devices. For example, the first reading means may be a non-contact fixed bar code scanner sensor, while the second reading means may be a photo-reflector. To detect the presence of a test pack effectively by means of the second reading means, the top seal of a test pack may be an aluminum foil for heat sealing having a high reflectivity of light or, a material having the surface painted in a light with color, or without letters or signs printed on the surface. The former two are generally preferred. In addition, different wave lengths are desirably used for the first and second reading means to prevent any interference.

The electronic control unit used according to the present invention generally comprises an input connected to the optical detecting means mounted on the movable scanning body of the x/y scanning mechanism, and an output connected to the transporting and stopping means for the carrying tray in the transporting channel and the driving mechanisms for the x/y scanning mechanism (driving for scanning in x and y directions, lifting of vacuum head, supplying suction to vacuum pad). In addition, the input of the electronic control unit is connected to an adequate signal input unit to specify the loading sequence of test packs onto the carrying tray. The electronic control unit generally comprises a microcomputer.

The input unit is used to specify an analyzing sequence of test packs for each specimen to be analyzed by an analyzing apparatus. The input init may be a ten-key or other keyboard or equivalent as used for any general computer system, or otherwise an external computer.

Preferably, the electronic control unit according to the present invention comprises a storage (internal memories) which stores the information on the conditions (such as positions, type, etc.) of each test pack in the test pack drawer, provided in the form of the detected signals from the optical detecting means, so as to make use of the stored information for the loading of test packs. In this case, it is desirable to update the stored information sequentially for the loading operation of each test pack.

DETAILED DESCRIPTION OF THE PREFERRED EMBODIMENT

Figure 1:
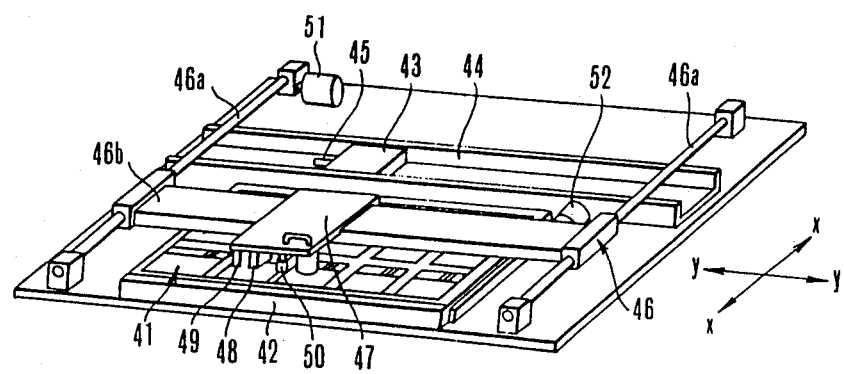
FIG. 1 is a perspective showing an embodiment of the selective test pack feeder for biochemical analyzing apparatus according to the present invention to illustrate its construction.
Figures 2, 3:
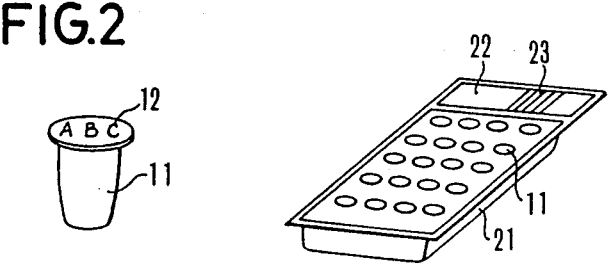
FIG. 2 is a perspective showing a test pack example to be transported by the embodiment of the present invention as shown in FIG. 1.
FIG. 3 is a perspective showing a test pack tray example as used in the embodiment as shown in FIG. 1.

In reference to FIG. 1 which is a perspective showing a preferred embodiment of the present invention to illustrate its construction, 41 is a group of test pack trays. Each test pack tray 21 contains many test packs 11 of same type to be used for the same analyte. The test pack 11 used in this embodiment, as shown in FIG. 2, is a top-opened cup type pack (black polypropylene or polystyrene pack of 8mm in inner bottom diameter and max. 14 mm in outer diameter, for example) which contains a given reagent lyophilized, which is heat-sealed with a laminated aluminum foil and sealed up with a top seal 12. In this embodiment, the surface of the top seal 12 is marked with an analyte name.

42 is a test pack drawer which contains the group of test pack trays 41 in a plane. Each test pack tray 21 contains many test packs 11 of the same type in arrays on the same level, as shown in FIG. 3. A bar code label 22 is attached on the top and end part of the test pack tray 21. In this embodiment, the bar code label 22 contains an analyte ID number of 2 digits and a lot ID number of 2 to 6 digits in an interleaved 2 of 5 coding format. However, the notation is not limitative. The test pack drawer 42 is supported by two rails, right and left, (not shown) so that it can be drawn out of the feeder (in the x direction as shown in FIG. 1) to place the group of test pack trays 41 in arrays in it.

In this embodiment, a sorter controller as described hereinafter is requested, for example, by means of a sense switch (not shown) for the pushed-in test pack drawer 42 to reform the map of test pack trays, when test packs are supplied in the test pack drawer 42.

44 is a transporting channel placed almost on the same level with the test pack drawer 42. In this embodiment, the channel 44 is a linear top-opened U-groove with two mobile belts (not shown) mounted on both sides of the channel bottom, on which the carrying tray is transported by the aid of frictional force. 45 is a stopper which can stop the carrying tray transported in the channel 44 to keep it at the test pack loading position. The stopper 45 can be moved by an advancing and reversing mechanism (not shown) between an advanced position and a retracted position in the transporting channel 44. In this embodiment, the stopper 45 stops the carrying tray at its advanced position, and returns to its retracted position to allow the carrying tray to be transferred in the channel 44.

The transport channel 44 is provided with a conveyor mechanism, for example, an elevator, attached to its top and bottom positions to connect the selective test pack feeder according to the invention to an analyzing apparatus. However, this conveyor mechanism is not shown here, because it is not directly related to the invention.

Figure 4:
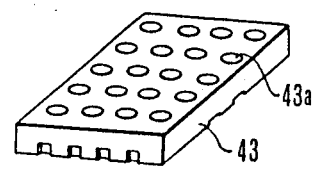
FIG. 4 is a perspective showing a carrying tray example as used in the embodiment as shown in FIG. 1.

43 is a carrying tray which is transported in the channel 44. The carrying tray 43 is provided with several arrays of top-opened holes 43a in which test packs are inserted, as shown in FIG. 4. The carrying tray 43 holding many test packs (fitted in the holes 43a) arrayed in a preset sequence is transported into the analyzing apparatus (not shown) where the test packs are then thermally controlled by an appropriate thermostatic device. Therefore, the carrying tray 43 has to be heat conductive. In this embodiment, the carrying tray 43 is of aluminum, which has a high heat conductivity. However, the material of the tray 43 is not limitative.

An x/ scanning mechanism 46 comprises a running plate 46b which is driven by a motor 51 for the x direction through a toothed belt (not shown) to run along a pair of guide rails 46a largely spaced in parallel, so as to make a scanning in the x direction as shown in FIG. 1. The running plate 46b is also equipped with a motor 52 to drive a scanning plate 47 in the y direction.

The plate 47 is a movable scanning body which is supported and driven by a driving mechanism (not shown) to run on the running plate 46b and scan in the y direction as shown in FIG. 1.

The movable scanning plate 47 is equipped with a vacuum head 50 (connected to an air suction controller, not shown) which removes a test pack 11 and places it in the carrying tray 43 at the specified position after the x and y scanning; a pack sensor (infrared photo-reflector) 49 which is the second reading means to detect the presence of the test pack 11; and a red-light bar code sensor 48 which is used as the first reading means to read the bar code label 22 on the test pack tray 21.

Figure 5:
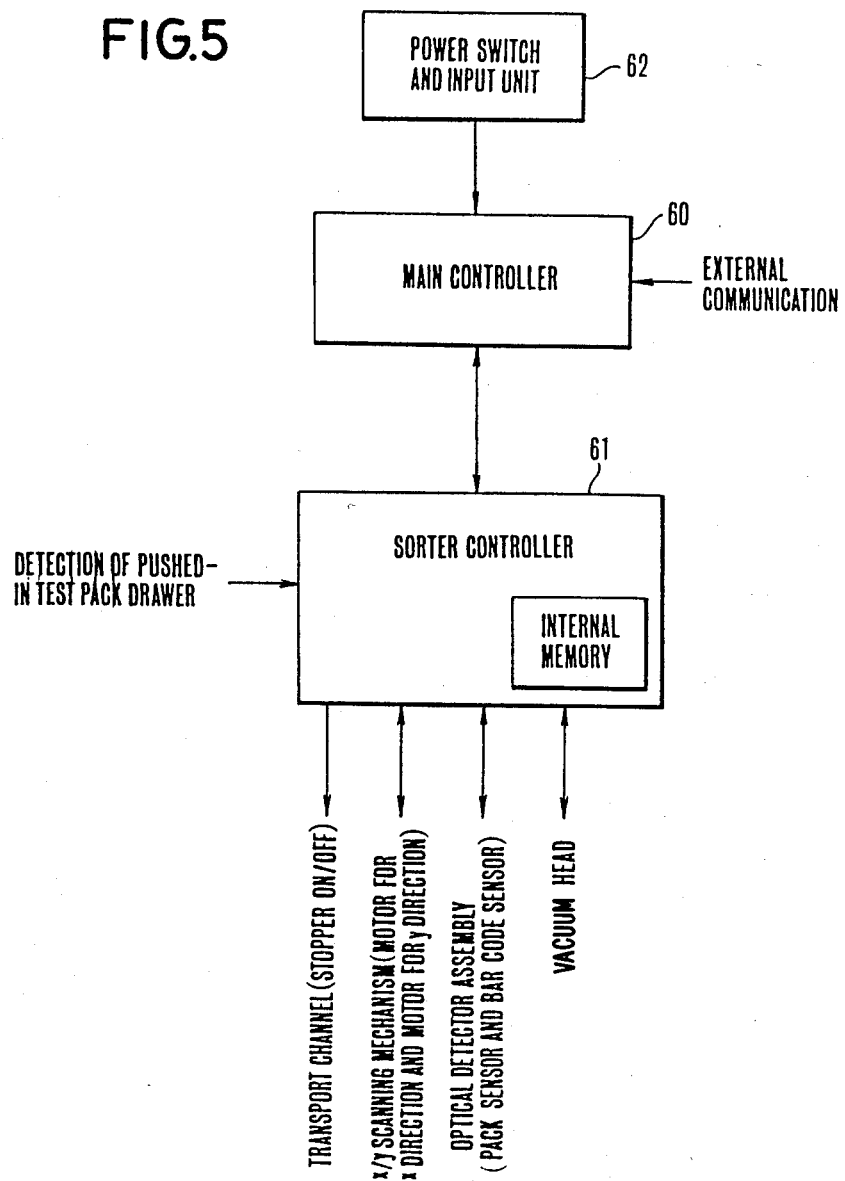
FIG. 5 is a block diagram showing the electronic control unit according to the present invention to illustrate its facilities.

The x/y scanning mechanism 46 also comprises driving mechanisms to make an x/y scanning, to lift the vacuum head, and to remove test packs to selectively load them into the carrying tray 43 in the preset sequence according to the signals coming from a sorter controller 61 in the electronic control unit as shown in FIG. 5.

Figure 6:
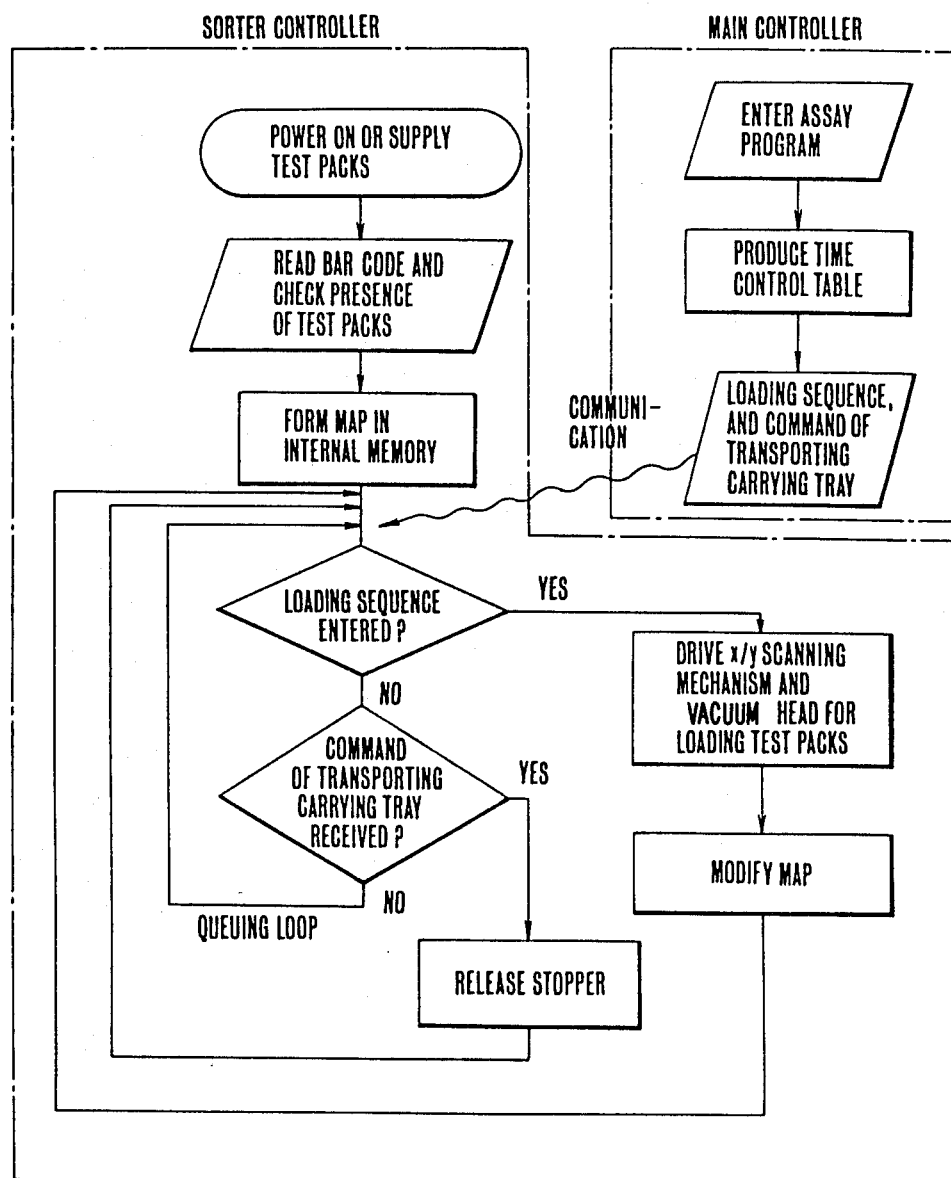
FIG. 6 is a flow chart to illustrate the operation of the sorter controller as shown in FIG. 5.

The control operation of the sorter controller 61 as shown in FIG. 5, used in this embodiment, is illustrated by FIG. 6 showing the flow chart of the operation.

When the feeder is powered on, or supplied with test packs, the sorter controller 61 reads the bar codes on the test pack trays and detects the presence of test packs to produce a map in the internal memory. When the loading sequence of test packs is then sent from the input unit 62 through the main controller 60, test packs are loaded onto the carrying tray 43 and the map in the memory is modified. While the command of transfer for the carrying tray 43 is being sent, the stopper 45 is temporarily released to enable the transfer of the carrying tray 43.

The operation of the selective test pack feeder in this embodiment thus constructed will be described below.

At first, the test pack drawer 42 is pulled out of the feeder body, and the required number of test pack trays 21 of required types is placed in the drawer, which is inserted again into the feeder body.

The bar code sensor 48 then reads the bar code on each of test pack trays 21 in the test pack drawer 42 while the x/y scanning mechanism is operating. The position and type of each test pack tray 21 are then stored in the internal memory in the sorter controller 61. At the same time, the presence of each test pack 11 in each test pack tray 21 is checked and stored in the internal memory in the sorter controller, while the x/y scanning mechanism is operating over the test pack trays 21.

Thus, the type of each test pack tray 21 set in the test pack drawer 42 at any preset position as well as the address of each test pack 11 in the test pack trays 21 is stored in the internal memory in the sorter controller 61. In other terms, a map showing the address and type of each test pack is stored in the internal memory.

Then, the sorter controller 61 receives a command (the loading sequence of test packs into the carrying tray 43) from the input unit 62, and drives the x/y scanning mechanism according to the input command to repeat the sequential operations of removing a test pack 11 in the test pack tray 21 at the prescribed position and transferring it in the carrying tray 43 at the prescribed loading position according to the map of test packs stored in the internal memory.

After test packs 11 have been loaded in the carrying tray 43, the map formed in the internal memory in the sorter controller 61 is sequentially modified (updated) so that the repetitive operations of scanning and loading can be rapidly performed and the consumption of test packs in the test pack drawer can be detected by reading the signals from the sorter controller 61.

The selective test pack feeder according to the invention provides for the mechanized and automatized loading of test packs selectively into the carrying tray 43 according to the random analysis requirements of many specimens, and it can be effectively matched with any automatic multi-analyte biochemical analyzing apparatus owing to its mechanized and automatized operation of loading test packs selectively and efficiently without any erroneous operation.

What is claimed is:

1. A selective test pack feeder for a biochemical analyzing apparatus, comprising: a channel (44) in which a carrying tray (43) for holding a matrix of test packs is transported and which is equipped with means (45) for stopping said carrying tray at a loading position; a test pack darwer (42) in which multiple types of test pack trays (21) holding many arrays of same type test packs (11) and labelled with the marking of said test pack type on the top face of said tray are placed in a plane on the same level with said transporting channel; an x/y scanning mechanism (46) disposed above both said transporting channel and said test pack drawer and equipped with a movable scanning body (47) driven by a driving mechanism (46a, 46b, 51, 52) to implement x/y scanning; an input unit (62) to specify a loading sequence of said test packs from said said test pack trays into said carrying tray; means (50) for engaging and removing said test packs and optical detecting means (48, 49) for detecting the presence of said test packs and for reading said marking of test pack type mounted on said movable scanning body of said x/y scanning mechanism, and an electronic control unit (60, 61) having an input connected to said optical detecting means and said input unit to specify a loading sequence of said test packs, and having outputs connected to said x/y scanning mechanism, to said engaging and removing means, and to said stopping means, said electronic control unit outputs controlling the selective transfer of said test packs from the test pack trays into the carrying tray.

2. A feeder according to claim 1 wherein said test pack comprise cups having planar seals over open upper ends thereof, and said engaging and removing means comprises a vacuum head for engaging said cup seals.

* * * * *